United States Patent [19]
Flora

[11] Patent Number: 5,434,506
[45] Date of Patent: Jul. 18, 1995

[54] EDDY CURRENT INSPECTION WITH STATIONARY MAGNETIC FIELDS AND SCANNING SENSOR ARRAYS

[75] Inventor: John H. Flora, Lynchburg, Va.

[73] Assignee: The Babcock & Wilcox Company, New Orleans, La.

[21] Appl. No.: 973,516

[22] Filed: Nov. 9, 1992

[51] Int. Cl.6 .................. G01N 27/82; G01R 33/12
[52] U.S. Cl. ........................ 324/242; 324/233; 324/262
[58] Field of Search .............. 324/240, 241, 242, 243, 324/239, 262, 207.18, 233, 234

[56] References Cited
U.S. PATENT DOCUMENTS

| | | | |
|---|---|---|---|
| 3,137,812 | 6/1964 | Andersen | 324/207.18 |
| 4,270,088 | 5/1981 | Weischedel | 324/242 |
| 4,445,088 | 4/1984 | Schubel | 324/240 |
| 4,594,549 | 6/1986 | Smith et al. | 324/242 |
| 4,651,093 | 3/1987 | Detriche et al. | 324/232 |
| 4,763,274 | 8/1988 | Junker et al. | 324/238 X |
| 4,931,730 | 6/1990 | Olsen et al. | 324/240 |
| 4,990,850 | 2/1991 | Votruba | 324/243 |
| 5,010,766 | 4/1991 | Typpo | 324/242 |
| 5,047,719 | 9/1991 | Johnson et al. | 324/242 |
| 5,117,185 | 5/1992 | Toomblom | 324/262 |

Primary Examiner—Sandra L. O'Shea
Assistant Examiner—J. M. Patidar
Attorney, Agent, or Firm—Daniel S. Kalka; Robert J. Edwards

[57] ABSTRACT

Defects such as corrosion located on a covered metal component are detected through Eddy current inspection using stationary magnetic fields and scanning sensors arrays. A magnetizing yoke is held fixed to the cover of the component and a magnetic flux sensor is used to scan the area between the legs of the yoke over the cover of the component. Also, a fixed array of sensors can be provided between the legs of the yoke for automatic multiplexing of the sensors and sampling in sequence of signal responses picked up by sensors in the sensor array. Additionally, a stationary magnetic field arrangement is provided by a plurality of probes aligned adjacent and parallel with each other. A fixed array of magnetic flux sensors are arranged between the legs of the aligned probes for scanning for defects. This arrangement of fixed sesnsors can be used for underwater use and sealed by a sealing compound. An attachment means can be used for holding the arrangement stationary with respect to the surface of a submerged component during sampling of the signal responses.

13 Claims, 4 Drawing Sheets

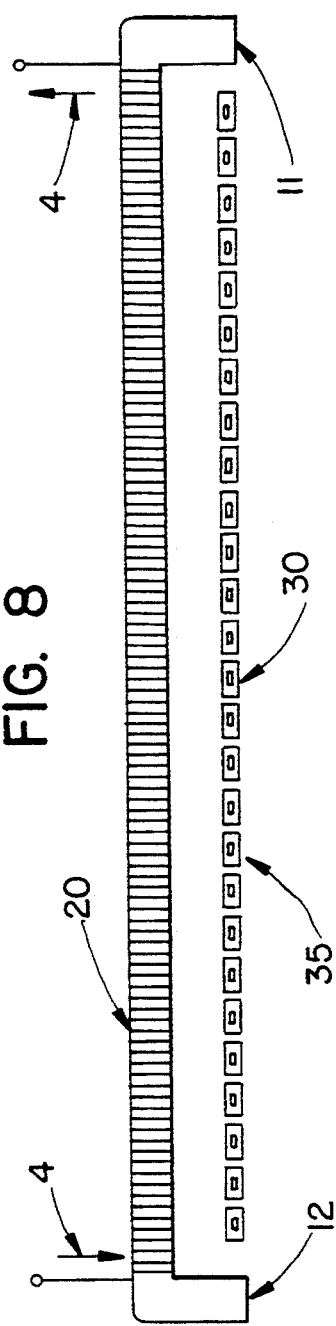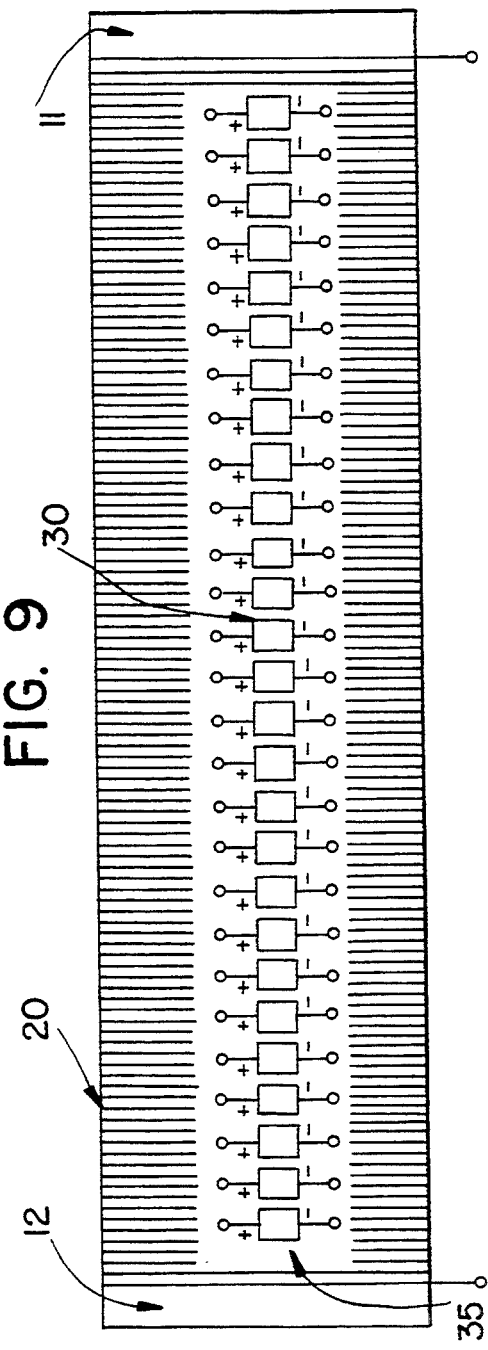

EDDY CURRENT INSPECTION WITH STATIONARY MAGNETIC FIELDS AND SCANNING SENSOR ARRAYS

BACKGROUND OF THE INVENTION

1. Field of the Invention

The present invention relates in general to the inspection of covered metal components and in particular to a new and useful method and device for the eddy current inspection of covered metal components using stationary magnetic fields and scanning sensor arrays.

2. Description of the Related Art

Corrosion on the exterior of components such as pipes, vessels and support structures is a pervasive problem throughout the petroleum and chemical process industry costing millions of dollars annually. A majority of these components are covered with material such as insulation which promote the corrosion by entrapment of water at the metal/cover interface. The removal of these covers and coatings for visual inspection is very costly and accounts for a substantial portion of the annual maintenance costs. Some methods have been developed in an effort to inspect covered components without removal of the insulation or covers.

One method developed for the inspection of pipes, tanks, and vessels through insulation is referred to as the Transient Electromagnetic Probe (TEMP). Two relevant patents have been issued; SPIES (U.S. Pat. No. 4,843,320) and Lara (U.S. Pat. No 4,843,319). This method uses the decay time of a diffusing eddy current pulse in the vessel wall to measure its thickness. The basic method is distinctly different from the low frequency eddy current (LOFEC) method in that transient decay time of diffusing eddy current is measured rather than flux field perturbations caused by a localized defect. Other distinguishing differences are:

1. TEMP measures the average wall thickness over a large ($\geq 16^4$ inch $\gamma$diameter)—LOFEC detects the loss of surface material due to corrosion under insulation (CUI) in areas as small as 1" diameter.

2. TEMP is not a scanning technique—the very large probe head must be left in place for about 3 seconds to make a single measurement. The LOFEC method can be scanned at least as fast as 4–6"/sec (probably faster) continuously producing output signals. Therefore, the LOFEC technique can be used as an inspection, as opposed to a sampling tool.

3. There is no evidence that the TEMP method can handle the significant "artifacts" that produce signal perturbations in electromagnetic testing—these are aluminum cover overlaps, carbon steel retaining wires under the aluminum, circumferential weld beads, hidden taps or plugs, nearby support brackets, steam trace lines, etc. The LOFEC method has been designed to eliminate or minimize the effects of all those artifacts.

A second method which has been developed for the CUI problem is the portable, real-time x-ray system (LIXI ®). Low energy x-rays are directed tangentially to the pipe so that they penetrate the insulation but not the pipe wall, thus imaging the corrosion area. This technique is much too slow to be used as an inspection tool to cover long lengths of pipe. The slow speed is due to a very limited field of view and the many tangential shots required to look at just one axial location on the pipe. It would be best suited to do spot checks for confirmation of corrosion damage after detection by a scanning method such as LOFEC. A second serious problem with the portable x-ray method is that scale in the corrosion site may tend to hide the corrosion damage.

However, these methods have major drawbacks. Particularly, ultrasonic inspection methods are severely limited by the need for fluid couplant, scattering of the ultrasound within the cover, air gap attenuation, mechanical alignment problems, and the poor resolution resulting from the relatively low operating frequencies required to penetrate the cover. Microwave techniques require removal of aluminum weather barriers, are adversely affected by moisture, and are scattered by insulation covers and by the shape of the corroded areas. X-radiation methods are time consuming, hazardous, relatively expensive, and are limited by the size and accessibility of the covered components.

In response to the deficiencies found in the methods listed above, the low frequency eddy current (LOFEC) method was developed for detecting corrosion and other defects on the surfaces of metal components that are covered with various materials such as paint, foam rubber, marine growth, calcium silicate insulation and relatively thin metal sheets. The object of the LOFEC method is to detect surface defects such as corrosion on the component while leaving the covering material intact.

FIGS. 1–5 illustrate a basic LOFEC probe generally designated 2 used for detection of surface defects such as corrosion under covers. The LOFEC probe depicted in FIGS. 1–5 comprises an inverted U-shaped yoke 10 having legs 11 placed on a cover 40 of a component 44 such as a steel plate. An excitation coil 20 is wound about the magnetizing yoke 10 between the legs 11. An alternating current 4 composed of one or more sinusoidal components is generated and applied to terminal 22 of the excitation coil 20. This alternating current 4 produces an alternating magnetic field 18 in the inverted U-shaped yoke 10. The yoke 10 guides the magnetic field through the cover 40 and into the component 44 beneath. If the component 44 is a ferromagnetic steel, the magnetic field 18 will be concentrated in the plate and directed from one leg of the yoke 10 toward the other. The alternating field 18 induces eddy currents 8 in the steel and other metals, (e.g., aluminum covers 40), located between the probe and the steel. The induced currents 8 tend to flow between and around the legs 11 of the U-shaped yoke 10 as illustrated in FIG. 1. Both the current 8 and the magnetic flux 18 are concentrated in the materials near and under the yoke 10.

FIG. 3 shows that a magnetic flux sensor 30 is located between the legs 11 of the U-shaped magnetizing yoke 10 beneath the excitation coil 20. The sensor 30 lies in a plane passing through the cross-section of the legs 11. The flux sensor 30 is an electronic device, such as a coil of conducting wire or a Hall element semiconductor that provides a signal response voltage proportional to the intensity of the magnetic flux 18 intercepted by the sensor 30. Under normal conditions, e.g., a uniform steel structure with no surface defects, the magnetic flux 18 and induced eddy currents 8 in the region directly under the excitation coil windings 20 are parallel to the plane formed by the sensor 30 that intersects the legs 11. The magnetic flux 18 flows from one leg 11 to the other and induced current 8 flows perpendicular to the flux 18. The presence of a near surface defect 55 in the steel component 44 such as corrosion causes a change in the magnitude, phase and direction of the induced currents 8 and associated magnetic field 18 within the steel 44 and in the region between the steel 44 and the probe 2.

Surface defects 55 are identified by scanning the probe 2 over the cover 40 of the structure 44 and detecting the signal response voltage, observed at terminals 33 of the flux sensor 30.

However, presently there is a need for a method or device for reducing or minimizing extraneous and unwanted signal responses caused by variations in the geometry and electromagnetic properties of the component 44 when using the LOFEC technique.

Additionally, there is a need for a method or device which can detect defects on metal components covered with marine growth while minimizing extraneous signal responses.

SUMMARY OF THE INVENTION

The present invention comprises a LOFEC method and device for detecting corrosion on a covered metal component while at the same time minimizing extraneous and unwanted signal responses. One embodiment of the present invention provides for a stationary magnetic yoke placed on the cover of a component having a movable magnetic flux sensor located between the legs of the stationary yoke for scanning the component for defects.

A second embodiment of the present invention provides for a stationary magnetic yoke having a fixed array of sensors provided between the legs of the yoke for scanning through multiplexing. The fixed array arrangement provides for automatic multiplexing and signal response sampling through the sensor array for detecting defects in the component.

A third embodiment of the present invention provides for a plurality of probes that are aligned side by side and parallel with each other for covering a large area of the covered component. A fixed array of magnetic flux sensors are used for scanning the cover of the component. This arrangement can be sealed with various compounds such as epoxy for underwater use to detect defects on metal tanks or pipes submerged in the water and covered with marine growth or other types of coverings.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiments of the invention are illustrated.

BRIEF DESCRIPTION OF THE DRAWINGS

In the drawings:

FIG. 8 is a front view of another embodiment of the present invention; and

FIG. 9 is a bottom view of the probe of FIG. 8.

DESCRIPTION OF THE PREFERRED EMBODIMENTS

Figure 1:
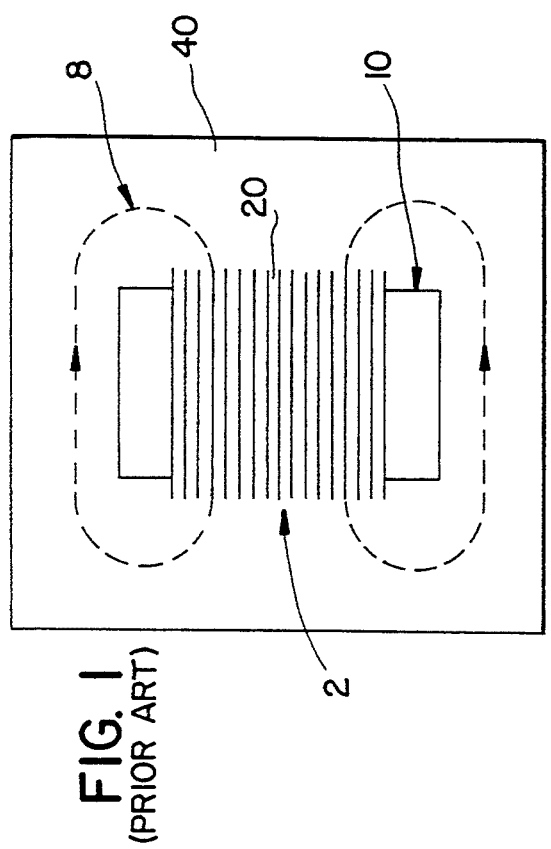
FIG. 1 is a top view of a known probe for a low frequency eddy current system.
Figure 3:
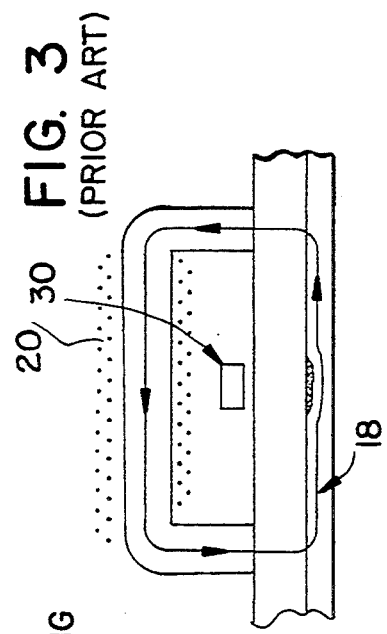
FIG. 3 is a cross-sectional front view of the probe of FIG. 1.
Figure 2:
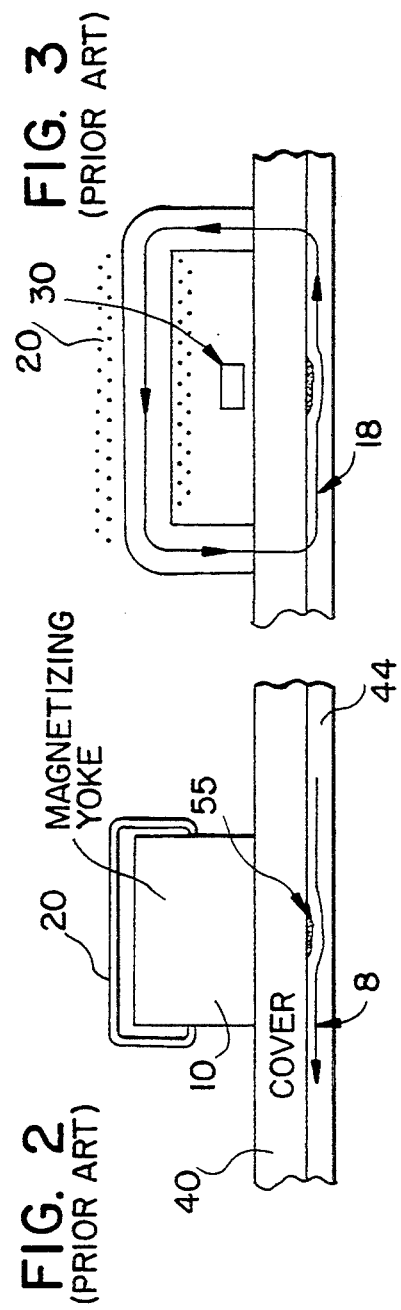
FIG. 2 is a side view of the probe of FIG. 1.
Figure 4:
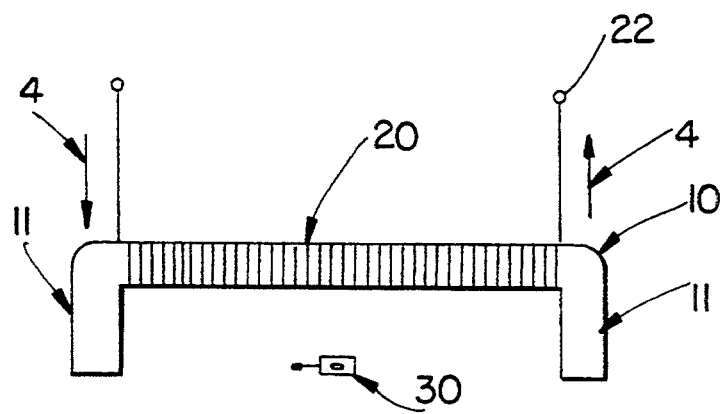
FIG. 4 is a partial front view of the probe of FIG. 1.
Figure 5:
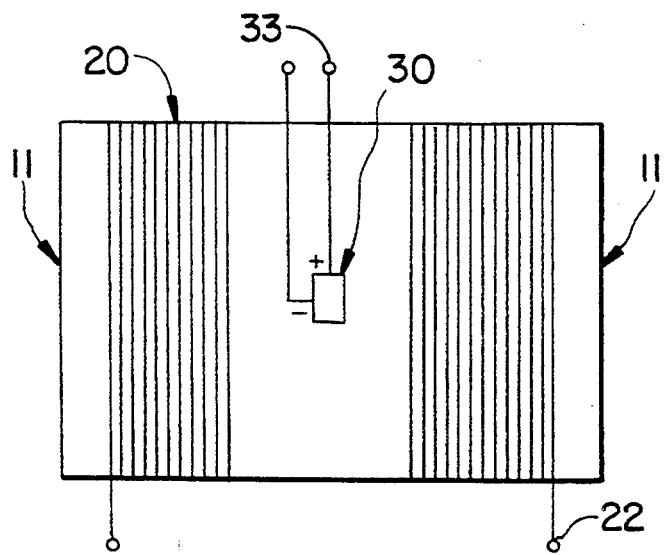
FIG. 5 is a bottom view of the probe of FIG. 1.

Throughout the drawings the same reference numerals are used to designate the same or similar parts.

Figure 6:
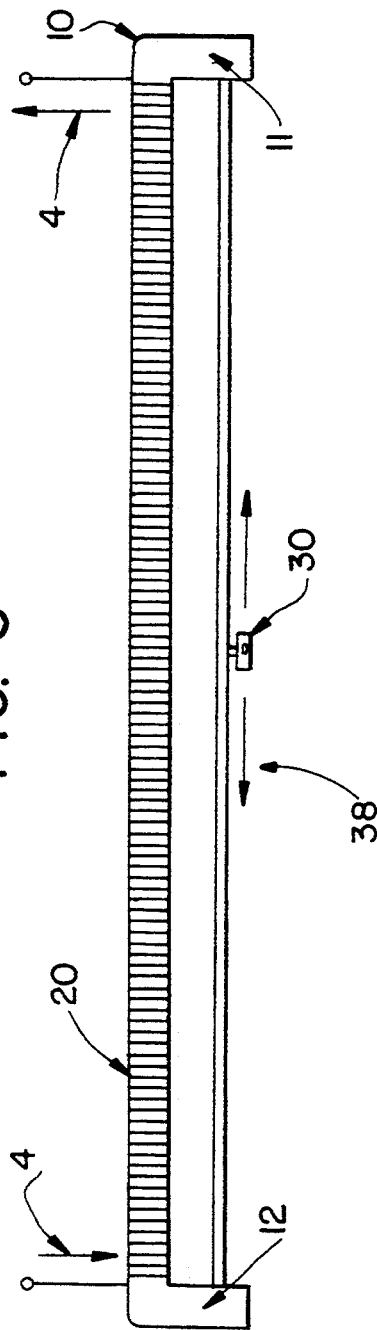
FIG. 6 is a front view of one embodiment of the present invention.
Figure 7:
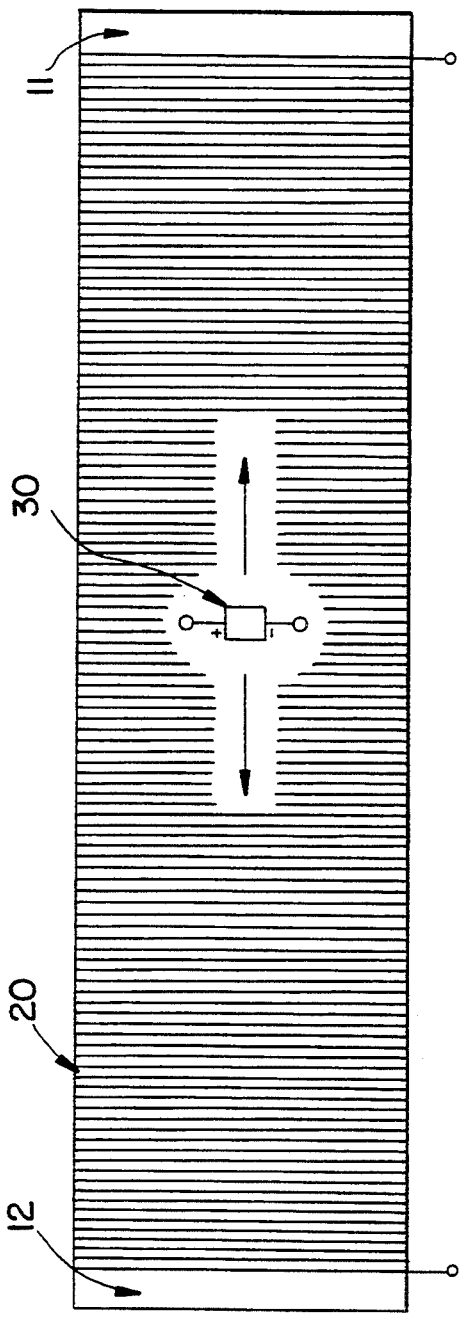
FIG. 7 is a bottom view of the probe of FIG. 6.

Referring to FIGS. 6 and 7, the invention illustrated therein comprises the basic LOFEC probe design with two major distinctions over the prior art. The legs 11, 12 of the yoke 10 are located at a great distance from each other greater than about six inches and can typically range from two to eight feet apart. A distance between each leg such as four or five feet allows for ample movement and scanning by a magnetic flux sensor 30 which is moved between each of the legs 11, 12 by a scanning means 38 such as stepper motors capable of moving sensor 30 either manually or automatically at a predetermined speed to a given location. Although the magnetizing yoke 10 remains fixed to the cover of a component, the magnetic flux sensor 30 is utilized to scan for defects of the component located between the legs 11, 12 of the yoke 10. A plurality of sensors 30 may be used in this configuration which includes a differential connection of pairs of magnetic flux sensors 30. The sensors 30 can be oriented in a plurality of directions beneath the excitation coil 20 and between the legs 11, 12.

FIGS. 8 and 9 illustrate a second embodiment of the present invention having a fixed array of sensors 35 provided between the legs 11, 12 of the yoke 10 for scanning by multiplexing, thereby allowing for the simultaneous transmission of signals picked up by the sensor array 35. This arrangement allows for the inspection of a large area of a covered component and is accomplished by placing the magnetizing yoke 10 against the cover of a component and performing automatic multiplexing and signal response sampling through the sensor array 35. The sensor array 35 comprises a plurality of magnetic flux sensors 30 arranged between the leg 11, 12 of the yoke 10.

The fixed array of sensors 35 allows for a reduction in the size and weight of the probe design found in the prior art as well as eliminates the moving parts, i.e., the yoke 10 and/or the magnetic flux sensors 30.

The configuration of the probe of the present invention can be sealed with various compounds such as epoxy for underwater use allowing the inspection of metal pipes and tanks located beneath the surface of the water. An attachment can be used to attach the probe arrangement to the surface of a component located under water.

The present invention has several advantages over other defect detecting devices and methods.

First, the present invention permits detection of defects such as corrosion found near the surface of components without removing the coatings and covers of the components.

Second, the present invention provides for a reduction in the size and weight of the scanning probe compared to that which would be required in order to scan both the magnetizing yoke 10 and the sensors 30 as a unit over a component.

Third, by providing stationary magnetic flux sensors in array 35 extending from one leg 11 of the magnetizing yoke 10 to the other leg 12 allows sampling in sequence of signal responses by using multiplexors for detecting changes in the magnetic flux caused by defects on the component. This arrangement thereby eliminates the requirement for moving parts such as the sensors 30 in order to inspect the component.

Fourth, a plurality of probes aligned adjacent and parallel to each other can cover large rectangular areas found on surfaces of tanks and pipes resulting in a reduction of time and cost normally needed for such inspections.

Fifth, the present invention, having a fixed array of magnetic flux sensors 35 allows for the sealing of the arrangement for underwater use by sealing means.

While specific embodiments of the invention have been shown and described in detail to illustrate the application of the principles of the invention, it will be understood that the invention may be embodied otherwise without departing from such principles.

What is claimed:

1. A device for detecting a defect on a metal component having a cover, the device comprising:
    a stationary magnetizing yoke having a body supported by at least two legs for contacting the cover and supporting the body over the cover thereby maintaining the yoke in a fixed position with a distance between each leg being greater than six inches;
    an excitation coil wound around the body of the yoke between the legs for receiving an alternating current and producing an alternating magnetic field through the yoke thereby inducing an eddy current through the component, the alternating magnetic field and the eddy current having a magnitude, a phase and a direction; and
    at least one magnetic flux sensor movable in an area between the excitation coil, the legs of the yoke and the cover of the component for scanning for changes in at least one of the magnitude, the phase and the direction of the alternating magnetic field and the eddy current for detecting a defect.

2. The device according to claim 1, wherein the at least one magnetic flux sensor includes two magnetic flux sensors which are differentially connected with respect to each other.

3. The device according to claim 1, wherein the distance between each leg ranges from 2' to 8' apart.

4. The device according to claim 3, wherein the distance between each leg is 4' to 5' apart.

5. A device for detecting a defect on a metal component having a cover located beneath the surface of the water, the device comprising:
    a stationary magnetizing yoke having a body supported by at least two legs, the legs for contacting the cover and supporting the body over the cover, the legs being at a distance greater than six inches from each other;
    an excitation coil wound around the body of the yoke between the legs for receiving an alternating current and producing an alternating magnetic field through the yoke thereby inducing an eddy current through the component, the alternating magnetic field and the eddy current having a magnitude, a phase and a direction;
    a fixed array of magnetic flux sensors positioned in an area between the excitation coil, the legs of the yoke and the cover of the component, the array of magnetic flux sensors for multiplexing in sequence the signal response retaining information which pertains to the magnitude, the phase, and the direction of the alternating magnetic field and the induced eddy currents; and
    means for sealing said yoke and sensors for underwater use.

6. The device according to claim 5, wherein the distance between each leg ranges from 2' to 8' apart.

7. The device according to claim 6, wherein the distance between each leg is 4' to 5' apart.

8. A method of detecting a defect on a metal component having a cover, the method comprising the steps of:
    placing a stationary magnetizing yoke on the cover of the component, the magnetizing yoke having a body supported by at least two legs, the legs for contacting the cover and supporting the body over the cover thereby maintaining the yoke in a fixed position with the legs having a distance between each other greater than six inches;
    winding an excitation coil around the body of the yoke;
    placing at least one magnetic flux sensor in an area between the excitation coil and the legs of the yoke over the cover of the component;
    applying an alternating current to the excitation coil for producing an alternating magnetic field through the yoke thereby inducing eddy currents through the component, both the alternating magnetic field and the eddy current having a magnitude, a phase and a direction; and
    moving the at least one magnetic flux sensor between the legs of the yoke over the cover of the component for monitoring the alternating magnetic fields and the eddy currents for changes in the magnitude, the phase and the direction.

9. The method according to claim 8, wherein the at least one magnetic flux sensor comprises a plurality of sensors movable between the legs of the yoke for monitoring the alternating magnetic field and the eddy current for changes in the magnitude, the phase and the direction.

10. The method according to claim 9, wherein the sensors are oriented in a plurality of directions.

11. The method according to claim 10, wherein the sensors are differentially connected with respect to each other.

12. The method according to claim 8, wherein the legs of the yoke have a distance between each other ranging from 2' to 8' apart.

13. The method according to claim 12, wherein the legs have a distance of between 4' to 5' apart.

* * * * *